US006235889B1

(12) United States Patent
Ulanovsky

(10) Patent No.: US 6,235,889 B1
(45) Date of Patent: May 22, 2001

(54) NUCLEIC ACID AMPLIFICATION USING MODULAR BRANCHED PRIMERS

(75) Inventor: Levy Ulanovsky, Westmont, IL (US)

(73) Assignee: University of Chicago, Chicago, IL (US)

( * ) Notice: Subject to any disclaimer, the term of this patent is extended or adjusted under 35 U.S.C. 154(b) by 0 days.

(21) Appl. No.: 09/264,466

(22) Filed: Mar. 8, 1999

Related U.S. Application Data

(63) Continuation of application No. 08/852,001, filed on May 6, 1997, which is a continuation-in-part of application No. 08/384,699, filed on Feb. 6, 1995, now Pat. No. 5,627,032, which is a continuation of application No. 07/810,898, filed on Dec. 20, 1991, now abandoned.

(51) Int. Cl.$^7$ .......................... C07H 21/04; C07H 21/02; C12Q 1/68; C12P 19/34; C12N 15/00

(52) U.S. Cl. ........................... 536/24.3; 536/23.1; 435/6; 435/91.2; 935/76; 935/77; 935/78

(58) Field of Search ...................... 435/91.2, 6; 536/23.1, 536/24.3; 935/76, 77, 78

(56) References Cited

U.S. PATENT DOCUMENTS

| 4,965,188 | 10/1990 | Mullis et al. ............................. 435/6 |
|---|---|---|
| 5,104,792 | * 4/1992 | Silver et al. .............................. 435/6 |
| 5,114,839 | 5/1992 | Blöcker .................................... 435/6 |
| 5,194,599 | * 3/1993 | Froehler et al. ................... 536/26.72 |
| 5,219,727 | 6/1993 | Wang et al. .............................. 435/6 |
| 5,451,503 | * 9/1995 | Hogan et al. ............................ 435/6 |
| 5,547,843 | 8/1996 | Studier et al. ........................... 435/6 |
| 5,573,905 | 11/1996 | Lerner et al. ............................ 435/6 |
| 5,624,798 | 4/1997 | Yamamoto et al. ..................... 435/6 |
| 5,624,802 | * 4/1997 | Urdea et al. ............................. 435/6 |
| 5,627,032 | 5/1997 | Ulanovsky ............................... 435/6 |
| 5,663,062 | 9/1997 | Sorge et al. ......................... 435/91.1 |
| 5,714,389 | 2/1998 | Charlton et al. ..................... 436/514 |

OTHER PUBLICATIONS

Aldhous, P. (1993) "A Faster Walk Along the Genome" *Science* 260: 1075.
Azhikina, T. et al. (1993) "Strings of Contiguous Modified Pentanucleotides with Increased DNA–Binding Affinityh Can Be Used for DNA Sequencing by Primer Walking," *Proc. Natl. Acad. Sci. USA.* 90: 11460–11462.
Beskin, A.D. et al. (1995) "On the Mechanism of the Modular Primer Effect," *Nucleic Acids Research* 23(15): 2881–2885.
Blöcker, H. and D.N. Lincoln. (1994) "The 'Shortmer' Approach to Nucleic Acid Sequence Analysis I: Computer Simulation of Sequencing Projects to Find Economical Primer Sets," *Cabios* 10(2): 193–197.
Cohen, A.S., et al. (1990) "Separation and Analysis of DNA Sequence Reaction Products by Capillary Gel Electrophoresis," *Journal of Chromatography* 516: 49–60.

Egholm, M., et al., (1993) "PNA Hybridizes to Complementary Oligonucleotides Obeying the Watson–Crick Hydrogen–Bonding Rules," *Nature* 365 (7): 566–568.
Guo, Z., et al. (1997) "Enhanced Discrimination of Single Nucleotide Polymorphisms by Artificial Mismatch Hybridization," *Nature Biotechnology* 15: 331–335.
Kieleczawa, J., et al. (1992) "DNA Sequencing by Primer Walking With Strings of Contiguous Hexamers," *Science* 258: 1787–1791.
Kotler, L., et al. (1994) "DNA Sequencing: Modular Primers for Automated Walking," *BioTechniques* 17 (3):554–558.
Kotler, L.E., et al. (1993) "DNA Sequencing: Modular Primers Assembled From a Library of Hexamers or Pentamers," *Proc. Natl.Acad. Sci.* 90: 4241–4245.
Leboeuf, R.D., et al. (1989) "Cloning and Sequencing of Immunoglobulin Variable–Region Genes Using Degenerate Oligodeoxyribonucleotides and Polymerase Chain Reaction," *Gene* 82: 371–377.
Leonits, N.B., et al., (1991) "Stability and Structure of Three–Way DNA Junctions Containing Unpaired Nucleotides," *Oxford University Press* 19 (4): 759–766.
Lu, M., et al. (1989) "DNase I Cleavage of Branched DNA Molecules," *The Journal of Biological Chemistry* 264 (35): 20851–20854.
Mathews, J.A. and L.J. Kricka, (1988) "Analytical Strategies for the Use of DNA Probes," *Analytical Biochemistry* 169: 1–25.
McCombie, W.R. and J. Kieleczaws (1994) "Automated DNA Sequencing Using 4–Color Fluorescent Detection of Reactions Primed with Hexamer Strings," *Bio Techniques* 17 (3): 574–579.
Nielsen, P.E., et al. (1991) "Sequence–Selective Recognition of DNA by Strand Displacement with a Thymine–Substituted Polyamide," *Science* (29): 1497–1500.
Nevinsky, G.A., et al. (1990) "Structure–Function Analysis of Mononucleotides and Short Oligonucleotides in the Priming of Enzymatic DNA Synthesis," *Biochemistry* 29: 1200–1207.
Ohtsuka, E., et al., (1985) "An Alternative Approach to Deoxyoligonucleotides as Hybridization Probes by Insertion of Deoxyinosine at Ambiguous Codon Positions," *The Journal of Biological Chemistry* 260 (5): 2605–2608.

(List continued on next page.)

*Primary Examiner*—Ethan Whisenant
(74) *Attorney, Agent, or Firm*—Barnes & Thornburg; Alice O. Martin

(57) ABSTRACT

Methods and compositions expand the options for making primers for use in amplifying nucleic acid segments. The invention eliminates the step of custom synthesis of primers for Polymerase Chain Reactions (PCR). Instead of being custom-synthesized, a primer is replaced by a combination of several oligonucleotide modules selected from a pre-synthesized library. A modular combination of just a few oligonucleotides essentially mimics the performance of a conventional, custom-made primer by matching the sequence of the priming site in the template. Each oligonucleotide module has a segment that matches one of the stretches within the priming site.

7 Claims, 9 Drawing Sheets

OTHER PUBLICATIONS

Raja, M.C., et al. (1997) "DNA Sequencing Using Differential Extension With Nucleotide Subsets (DENS)," Oxford University Press 25(4): 800–805.

Studier, F.W. (1989) "A Strategy for High–Volume Sequencing of Cosmid DNAs: Random and Directed Priming With a Library of Oligonucleotides," *Proc. Natl. Acad. Sci.* 86: 6917–6921.

Szybalski, W. (1990) "Proposal for Sequencing DNA Using Ligation of Hexamers to Generate Sequential Elongation Primers (SPEL–6)," *Gene* 90: 177–178.

Ulanovsky, L., et al. (1986) "Curved DNA: Design, Synthesis, and Circulation," *Proc. Natl. Acad. Sci.* 83: 862–866.

Ulanovsky, L., et al. (1990) "DNA Trapping Electrophoresis," *Nature* 343 (6254): 190–192.

Ulanovsky, L., et al. (1987) "Estimation of Wedge Components in Curve DNA," *Nature* 326 (16): 720–722.

Ulanovsky, L., et al. (1990) "DNA Trapping Electrophoresis," *Nature* 343(11): 190–192.

Walker T.G., et al. (1992) "Strand Displacement Amplification—an Isothermal, in vitro DNA Amplification Technique," Oxford University Press 20 (7): 1691–1696.

Walker, G.T., et al. (1993) "Empirical Aspects of Strand Displacement Amplification," Cold Spring Harbor Laboratory Press 9803 (93): 1–6.

Watson, J.D., et al. "Molecular Biology of the Gene," The Benjamin/Cummings Publishing Company, Inc.

Cooper et al., PNAS 86 :7336–7340 (1989).*

Guo et al., Biochemistry 29 : 570–578 (1990).*

Mueller et al., PNAS 85 : 9441–9445 (1988).*

Murchie et al., Nature 341 : 763–765 (1989).*

* cited by examiner

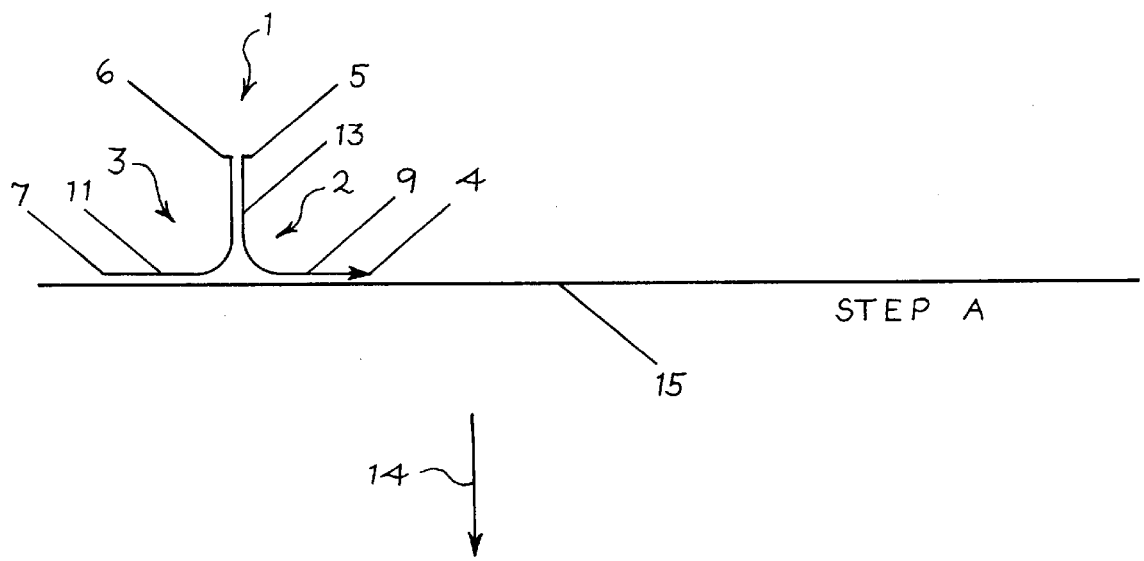
STEP A
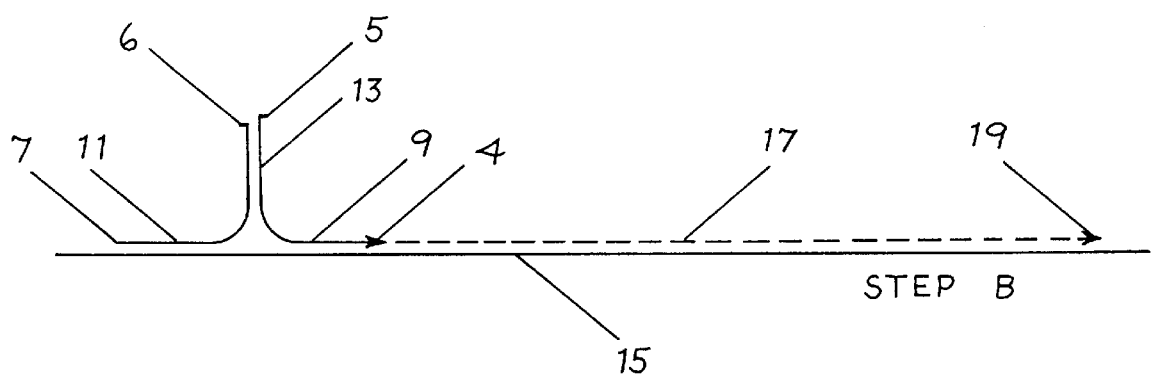
STEP B
TO FIG. 1(2)

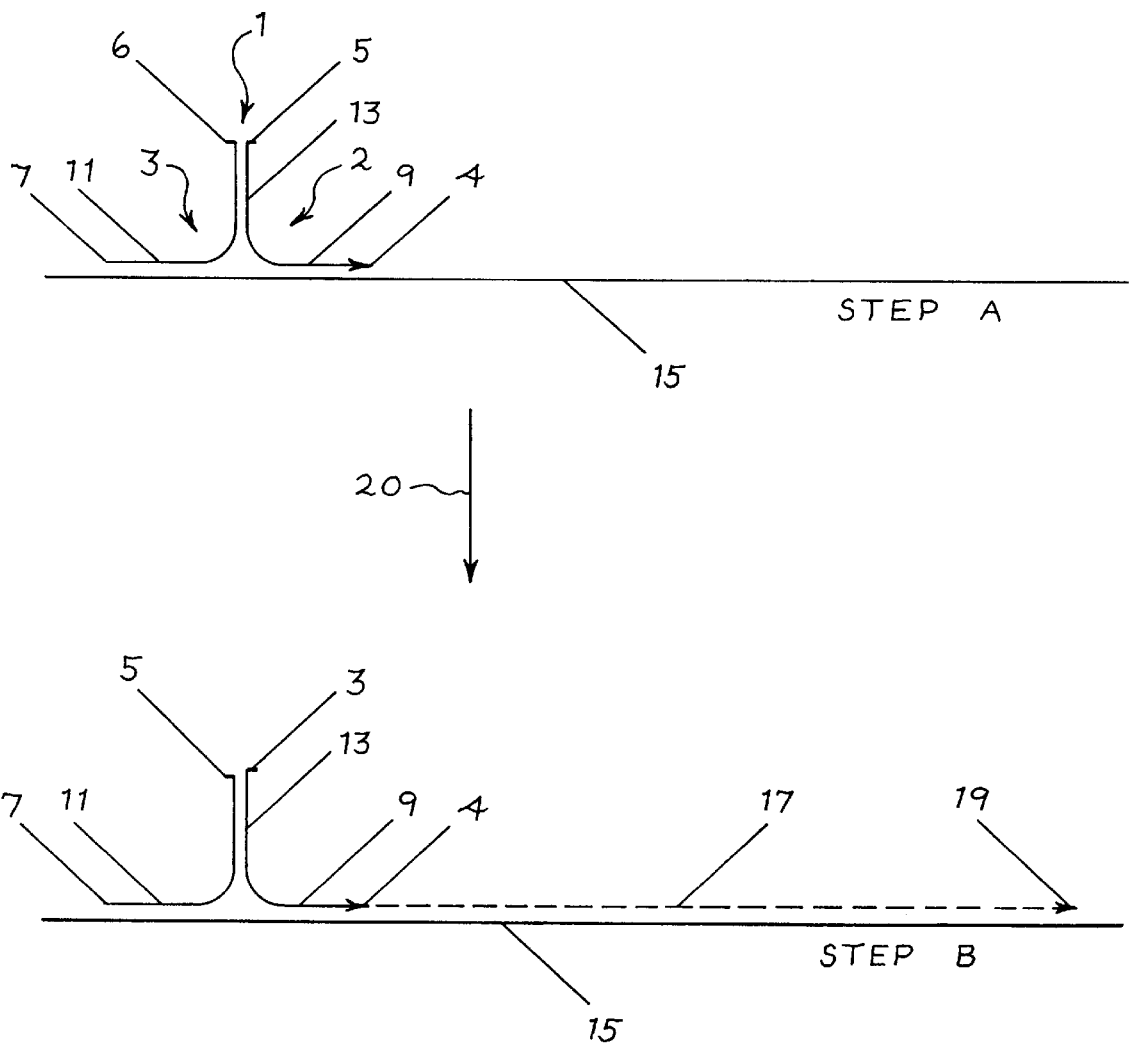

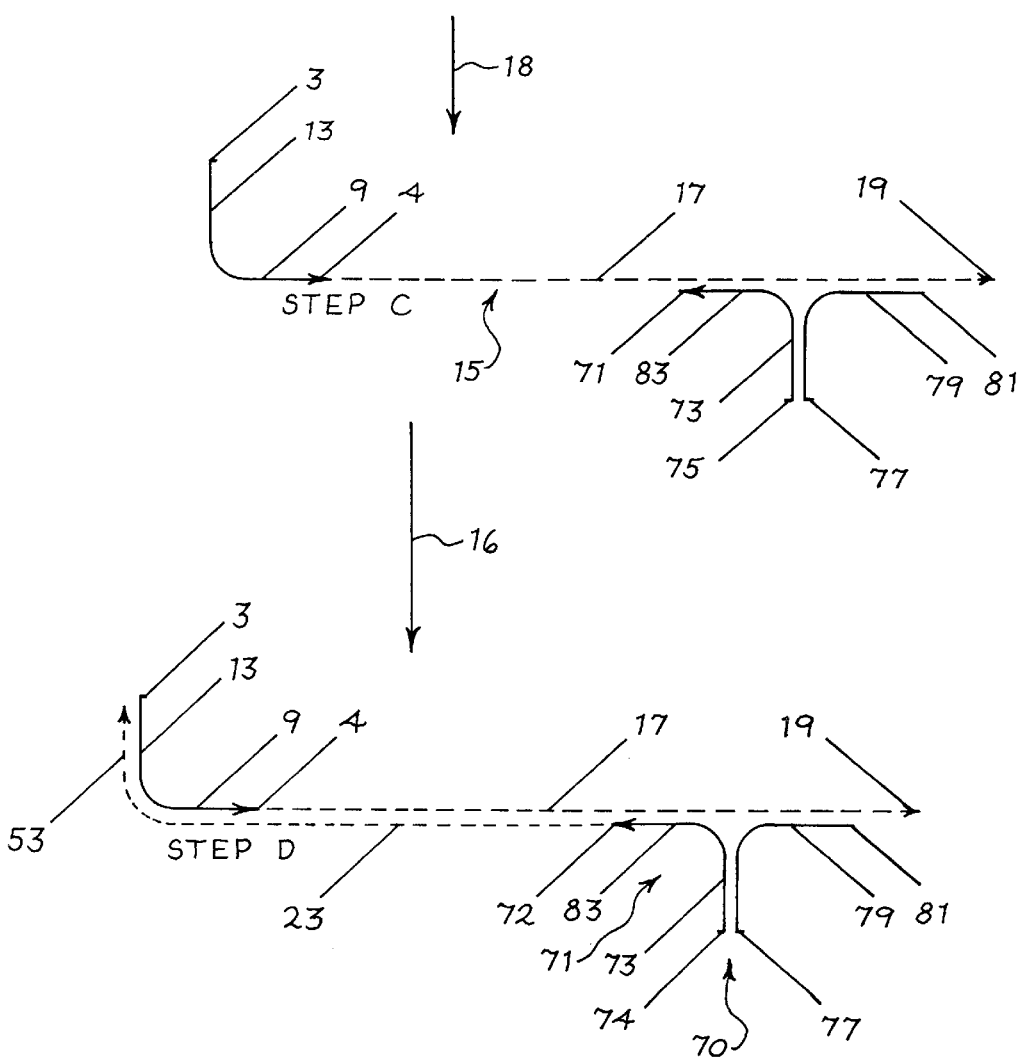

SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:1:

TCTTACGGTA ATCCATTGTA CTGCCGGACC AC                                    32

(2) INFORMATION FOR SEQ ID NO:2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: misc_feature
        (B) LOCATION: 17..18
        (D) OTHER INFORMATION: /product= "N = inosine"

(xi) SEQUENCE DESCRIPTION: SEQ ID NO:2:

ACGGGTACGA CGTTCANNAT TACC                                             24

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
            (A) NAME/KEY: misc_feature
            (B) LOCATION: 1
            (D) OTHER INFORMATION: /product= "N = inosine"

(ix) FEATURE:
            (A) NAME/KEY: misc_feature
            (B) LOCATION: 8
            (D) OTHER INFORMATION: /product= "N = inosine"

(xi) SEQUENCE DESCRIPTION: SEQ ID NO:3:

NCAGTACNCG AACGTCGTAC CCG                                              23

(2) INFORMATION FOR SEQ ID NO:4:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(ix) FEATURE:
            (A) NAME/KEY: misc_feature
            (B) LOCATION: 16..17
            (D) OTHER INFORMATION: /product= "N = inosine"

(ix) FEATURE:
            (A) NAME/KEY: misc_feature
            (B) LOCATION: 19..20
            (D) OTHER INFORMATION: /product= "N = inosine"

(xi) SEQUENCE DESCRIPTION: SEQ ID NO:4:

TGTACGACGT TCAGGNNTNN CGT                                              23

(2) INFORMATION FOR SEQ ID NO:5:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(ix) FEATURE:
            (A) NAME/KEY: misc_feature
            (B) LOCATION: 18..19
            (D) OTHER INFORMATION: /product= "N = inosine"

(xi) SEQUENCE DESCRIPTION: SEQ ID NO:5:

CTGACGTTCA GGGGTGGNNT AA                                               22

(2) INFORMATION FOR SEQ ID NO:6:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:6:

GTGGTCCGGC AGTACAATGG                                                  20

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:7:

ACGGGTACGA CGTTCAGG                                                    18

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:8:

TTTACTGCCA TATTCTCCCC ACAAAAAAGC                                        30

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: misc_feature
        (B) LOCATION: 17..18
        (D) OTHER INFORMATION: /product= "N = inosine"

(xi) SEQUENCE DESCRIPTION: SEQ ID NO:9:

ACGGGTACGA CGTTCANNTA TGGC                                             24

(2) INFORMATION FOR SEQ ID NO:10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: misc_feature
        (B) LOCATION: 8
        (D) OTHER INFORMATION: /product= "N = inosine"

(xi) SEQUENCE DESCRIPTION: SEQ ID NO:10:

NTGTGGGNCG AACGTCGTAC CCG                                              23

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single (D) TOPOLOGY: linear (ii) MOLECULE TYPE: other nucleic acid
        (A) DESCRIPTION: /desc = "primer"

(ix) FEATURE:
        (A) NAME/KEY: misc_feature
        (B) LOCATION: 16..17
        (D) OTHER INFORMATION: /product= "N = inosine"

(ix) FEATURE:
        (A) NAME/KEY: misc_feature
        (B) LOCATION: 19..20
        (D) OTHER INFORMATION: /product= "N = inosine"

(xi) SEQUENCE DESCRIPTION: SEQ ID NO:11:

TGTACGACGT TCAGGNNTNN CAG                                           23

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: misc_feature
        (B) LOCATION: 18..19
        (D) OTHER INFORMATION: /product= "N = inosine"

(xi) SEQUENCE DESCRIPTION: SEQ ID NO:12:

TAGACGTTCA GGGGTGGNNG TA                                            22

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:13:

TTTGTGGGGT GAATATGGCA G                                             21

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:14:

ACGGGTACGA CGTTCAGG                                                 18

(2) INFORMATION FOR SEQ ID NO:15:

(i) SEQUENCE CHARACTERISTICS:
        (A) LENGTH: 31 base pairs
        (B) TYPE: nucleic acid
        (C) STRANDEDNESS: single (D) TOPOLOGY: linear (ii) MOLECULE TYPE: other nucleic acid
        (A) DESCRIPTION: /desc = "primer"

(xi) SEQUENCE DESCRIPTION: SEQ ID NO:15:

AGTACGGTCA GTACAGTGTC ATCCTGCAGG T                                          31

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: misc_feature
        (B) LOCATION: 17..18
        (D) OTHER INFORMATION: /product= "N = inosine"

(xi) SEQUENCE DESCRIPTION: SEQ ID NO:16:

ACCCGCTATC TGTGCANNAC TGAC                                                  24

(2) INFORMATION FOR SEQ ID NO:17:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: misc_feature
        (B) LOCATION: 1
        (D) OTHER INFORMATION: /product= "N = inosine"

(ix) FEATURE:
        (A) NAME/KEY: misc_feature
        (B) LOCATION: 8
        (D) OTHER INFORMATION: /product= "N = inosine"

(xi) SEQUENCE DESCRIPTION: SEQ ID NO:17:

NGATGACNCG CACAGATAGC GGG                                                   23

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: misc_feature
        (B) LOCATION: 15
        (D) OTHER INFORMATION: /product= "N = inosine"

(ix) FEATURE:
        (A) NAME/KEY: misc_feature
        (B) LOCATION: 17..18
        (D) OTHER INFORMATION: /product= "N = inosine"

(xi) SEQUENCE DESCRIPTION: SEQ ID NO:18:

```
GCTATCTGTG CAGGNTNNCC G                                              21

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: misc_feature
        (B) LOCATION: 17..18
        (D) OTHER INFORMATION: /product= "N = inosine"

(xi) SEQUENCE DESCRIPTION: SEQ ID NO:19:

GTCTGTGCAG GGGTGGNNGT A                                              21

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:20:

CCAGGATGAC ACTGTACTGA C                                              21

(2) INFORMATION FOR SEQ ID NO:21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:21:

ACCCGCTATC TGTGCAGG                                                  18

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:22:

TCATCAGAAA CGAACGCATC ATCAAGTGCC                                     30

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
```

(D) TOPOLOGY: linear (ii) MOLECULE TYPE: other nucleic acid
            (A) DESCRIPTION: /desc = "primer"

(ix) FEATURE:
            (A) NAME/KEY: misc_feature
            (B) LOCATION: 17..18
            (D) OTHER INFORMATION: /product= "N = inosine"

(xi) SEQUENCE DESCRIPTION: SEQ ID NO:23:

ACCCGCTATC TGTGCANNCG TTTC                                                  24

(2) INFORMATION FOR SEQ ID NO:24:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(ix) FEATURE:
            (A) NAME/KEY: misc_feature
            (B) LOCATION: 1
            (D) OTHER INFORMATION: /product= "N = inosine"

(ix) FEATURE:
            (A) NAME/KEY: misc_feature
            (B) LOCATION: 8
            (D) OTHER INFORMATION: /product= "N = inosine"

(xi) SEQUENCE DESCRIPTION: SEQ ID NO:24:

NGATGATNCG CACAGATAGC GGG                                                   23

(2) INFORMATION FOR SEQ ID NO:25:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(ix) FEATURE:
            (A) NAME/KEY: misc_feature
            (B) LOCATION: 16..17
            (D) OTHER INFORMATION: /product= "N = inosine"

(ix) FEATURE:
            (A) NAME/KEY: misc_feature
            (B) LOCATION: 19..20
            (D) OTHER INFORMATION: /product= "N = inosine"

(xi) SEQUENCE DESCRIPTION: SEQ ID NO:25:

AGCTATCTGT GCAGGNNTNN CTG                                                   23

(2) INFORMATION FOR SEQ ID NO:26:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(ix) FEATURE:

(A) NAME/KEY: misc_feature
          (B) LOCATION: 17..18
          (D) OTHER INFORMATION: /product= "N = inosine"

(xi) SEQUENCE DESCRIPTION: SEQ ID NO:26:

GTCTGTGCAG GGGTGGNNGA T                                              21

(2) INFORMATION FOR SEQ ID NO:27:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "primer"

(xi) SEQUENCE DESCRIPTION: SEQ ID NO:27:

ACTTGATGAT GCGTTCGTTT CT                                             22

(2) INFORMATION FOR SEQ ID NO:28:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "primer"

(xi) SEQUENCE DESCRIPTION: SEQ ID NO:28:

ACCCGCTATC TGTGCAGG                                                  18

(2) INFORMATION FOR SEQ ID NO:29:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "primer"

(ix) FEATURE:
          (A) NAME/KEY: misc_feature
          (B) LOCATION: 16..17
          (D) OTHER INFORMATION: /product= "N = inosine"

(xi) SEQUENCE DESCRIPTION: SEQ ID NO:29:

CCATGCCGAT GTCGGNNCCT GAT                                            23

(2) INFORMATION FOR SEQ ID NO:30:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "primer"

(ix) FEATURE:
          (A) NAME/KEY: misc_feature
          (B) LOCATION: 18..19
          (D) OTHER INFORMATION: /product= "N = inosine"

(ix) FEATURE:

```
            (A) NAME/KEY: misc_feature
            (B) LOCATION: 21..22
            (D) OTHER INFORMATION: /product= "N = inosine"

(xi) SEQUENCE DESCRIPTION: SEQ ID NO:30:

CCATGCCGAT GTCGGGGNNT NNTGG                                            25

(2) INFORMATION FOR SEQ ID NO:31:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(ix) FEATURE:
            (A) NAME/KEY: misc_feature
            (B) LOCATION: 23..24
            (D) OTHER INFORMATION: /product= "N = inosine"

(xi) SEQUENCE DESCRIPTION: SEQ ID NO:31:

CCATGCCGAT GTCGGGGGGT GGNNGGC                                          27

(2) INFORMATION FOR SEQ ID NO:32:

(i) SEQUENCE CHARACTERISTICS:
            (A) LENGTH: 62 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:32:

CAGTACTAGA CTAGACTAGA CTAGACGATA GTATAGCCCA TCAGGCCCCG ACATCGGCAT      60

GG                                                                    62

(2) INFORMATION FOR SEQ ID NO:33:

(i) SEQUENCE CHARACTERISTICS:
            (A) LENGTH: 62 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:33:

CAGTACTAGA CTAGACTAGA CTAGACGATA GTATAGCCCA CCACCCCCG ACATCGGCAT       60

GG                                                                    62

(2) INFORMATION FOR SEQ ID NO:34:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:34:
```

```
GCTATCTGTG CAAAACCG                                              18

(2) INFORMATION FOR SEQ ID NO:35:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:35:

ACCAGAGGCA CAGATA                                                16

(2) INFORMATION FOR SEQ ID NO:36:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:36:

TGCGTTTCCT CGGTTTCCTT CTGGTAACTT TGTTCGGCTA T                    41

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: misc_feature
        (B) LOCATION: 13..14
        (D) OTHER INFORMATION: /product= "N = inosine"

(xi) SEQUENCE DESCRIPTION: SEQ ID NO:37:

GCTATCTGTG CANNACCGAG                                            20

(2) INFORMATION FOR SEQ ID NO:38:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: misc_feature
        (B) LOCATION: 13..14
        (D) OTHER INFORMATION: /product= "N = inosine"

(xi) SEQUENCE DESCRIPTION: SEQ ID NO:38:

GCTATCTGTG CANNACCGA                                             19

(2) INFORMATION FOR SEQ ID NO:39:
```

```
    (i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:39:

TGACTCCATG GCCCAGAGGC ACAGATA                                              27

(2) INFORMATION FOR SEQ ID NO:40:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:40:

CAAAGAGCAT GGAGT                                                           15
```

NUCLEIC ACID AMPLIFICATION USING MODULAR BRANCHED PRIMERS

This is a continuation of copending U.S. Ser. No. 08/852,001, filed May 6, 1997, which is a continuation-in-part of U.S. Ser. No. 08/384,699 filed Feb. 6, 1995, now U.S. Pat. No. 5,627,032 which is a continuation of U.S. Ser. No. 07/810,898 filed Dec. 20, 1991 now abandoned.

The U.S. Government has rights to the invention pursuant to Contract W-31-109-ENG between the U.S. Department of Energy and the University of Chicago representing Argonne National Laboratory.

The invention provides methods and compositions that eliminate the need for custom synthesis of primers used in methods of amplifying nucleic acid segments such as the Polymerase Chain Reactions (PCR). Instead of being custom-synthesized, a primer is replaced by a combination of several branched and/or covered oligonucleotide modules selected from a pre-synthesized library. A modular combination of just a few oligonucleotides essentially mimics the performance of a conventional, custom-made primer by matching a sequence of a priming site in a template.

There are growing needs to perform hundreds and thousands and in the near future—tens of thousands, and perhaps millions of different amplification (e.g. PCR) reactions in areas as genome mapping, biomedical research and clinical diagnostics. In genome mapping, the locations of thousands of markers are being determined relative to each other and to such clones as YACs, cosmids, BACs and PACs. These locations are continuously updated by performing many different PCR reactions, each corresponding to a different marker, because the number of available markers and clones is growing rapidly. In biomedical research, with the explosive growth of the number of known genes related to various diseases, the need to screen a large number of mutations in many genes simultaneously will very soon require prohibitively large numbers of different PCR reactions to be performed for determining the effect of the various mutations on the diseases. With the number of fully sequenced genomes growing rapidly and including human sequences, simultaneous comprehensive polymorphism tests of thousands of genes is likely. Large scale screening will then be required for each individual to test predisposition for various genetic conditions.

One of the limitations of the present methods is the need to prepare large numbers of customized primers. Rather than synthesizing primers specifically for each reaction, a presynthesized library could be made. However, maintenance and management of a library that contains many thousands of customized primers is a bottleneck, for example in genome mapping. About a million primers will be required in the near future for genome-wide mutation screening. Management of such a huge library is very difficult. One alternative, cheap de novo synthesis of primers each time they are needed, may in the future be viable for small number of primers, at best-thousands of primers at a time. For much larger numbers of primers, this alternative is prohibitively expensive. Manual handling of great numbers of PCR reactions is exceedingly difficult. Dedicated robots are already under development for this purpose. In this instrumentation development, the main outstanding problems are synthesis, storage and handling of a large number of different PCR primers.

Almost a million-fold discrepancy between the scale of primer synthesis (1.0 $\mu$mol) and the amount of primer required for a conventional PCR reaction (2.0 pmol) could be alleviated using a pre-synthesized library of possible primer sequences. Such a library could be aliquoted into thousands of copies for individual users, thus dramatically slashing the expense per reaction and making the primers instantly available. However the number of samples (sequences) in such a library would be too large to be practical. For example, even the shortest primer expected to be unique in a plasmid-sized template, a nonamer, would require a quarter of a million sequences to be prepared, each in a separate receptacle.

New approaches to nucleic acid amplification are needed that are economical and can be scaled up and automated.

SUMMARY OF THE INVENTION

The methods and compositions of the present invention eliminate the need for custom primer synthesis in methods to amplify nucleic acid segments, e.g., the polymerase chain reaction (PCR). One aspect of the invention makes it possible to instantly assemble a primer of a given sequence using a pre-synthesized, modular, oligonucleotide library. Modular primers may be branched or covered. Branched primers have a three dimensional structure that is basically a three-way junction when annealed to a template. Covered primers are similar except for the absence of one portion of the junction. The stem portions of branched primers are constant and bind portions of variable modules together to give specificity to the initial priming (extension) yet allow amplification using conventional primers to proceed.

The invention is directed to methods and compositions for amplifying a segment of a nucleic acid template, in particular by a polymerase chain reaction. The method includes annealing the template to a first branched primer which includes both front and back oligonucleotide modules. "Front" refers herein to the 3' extending (downstream) sequence and "back" refers to the 5' end (upstream), both terms are in reference to the direction of extension of a sequence by the polymerase. Each oligonucleotide module sequence has a nucleotide sequence designated the stem segment. The stem segment sequences of the front and back oligonucleotide modules are complements of each other, and therefore are capable of annealing to each other. The stem segments when annealed form the stem of a branched primer.

The two oligonucleotide modules (front and back) also have an "arm segment" which is complementary to a nucleotide sequence site in a template. A "template" is a nucleic acid segment, a part of which is to be amplified. The sites to which the two arm segments are complementary are sufficiently close to each other in the template so that the first branched primer forms a 3-way junction when annealed to the template. The arm of the front oligonucleotide module of the first branched primer is extended on the template by a polymerase enzyme to form a first initial extension strand. The first initial extension strand is then annealed to a reverse primer which may be either branched (a second branched primer) or not and which is extended on the first initial extension strand by a polymerase enzyme to form a second. initial extension strand. The second initial extension strand is amplified by using amplification primers that include a reverse primer and/or at least one primer homologous to the stem sequence of the first and/or second branched primer. The arm of each oligonucleotide module sequence preferably contains at least one artificial base to reduce steric hindrance that may be caused by proximity of the stem to the extension point and/or to enhance the annealing stability. An intercalator group is optionally linked to an arm to stabilize the annealing of the arm to the template. Two examples of intercalators to stabilize the annealing are 1) acridine, and 2) 2-methoxy-6-chloro-9-aminoacridine.

Optionally, at least one of the back modules of the amplification primers is a 3' protruding sequence, i.e., when annealed to its priming site, the primer covers one or more extra bases in this site as compared to the front module. The iprotruding amplification primers preferably comprise artificial non-discriminating bases in order to reduce the number of possible sequences of these primers (the size of primer library.)

The invention relates a method for amplifying a segment of a nucleic acid template, said method comprising:

a. annealing the template to a first branched primer, said primer comprising a front and a back oligonucleotide module, wherein (i) the front oligonucleotide module comprises a stem segment, and (ii) wherein said stem segment is complementary to a stem segment of the back oligonucleotide module, and (iii) wherein said oligonucleotide modules anneal to each other by means of said stem segments; (iv) wherein each of said oligonucleotide modules also comprises an arm segment, and (v) wherein said segment is complementary to a site in the template, and (vi) wherein the two sites are sufficiently close to each other in the template so that said first branched primer forms a 3-way junction when annealed to the template;

b. extending the arm of the front module of the first branched primer cn the template by a polymerase enzyme to form a first initial extension strand;

c. annealing the first initial extension strand to a reverse primer which is extended on the first initial extension strand by a polymerase enzyme to form a second initial extension strand, said strand complementary to the first module of the first branched primer; and d. amplifying the second initial extension strand by using amplification primers.

An aspect of the invention is a method for amplifying a segment of a nucleic acid template by a polymerase chain reaction. The method includes the following steps:

a. annealing the template to a first branched primer comprising a front and a back module, each of said modules comprising a stem segment complementary to a stem segment in the other module. The modules are capable of annealing to each other via said stem segments to form a stem of the primer. Each module also comprises an arm segment which is complementary to a site in the template. The two sites corresponding to the two modules are positioned sufficiently close to each other in the template so that said branched primer annealed to the template forms a 3-way junction;

b. extending the arm of the front module of the first branched primer on the template by a polymerase enzyme to form a first initial extension strand;

c. annealing the first initial extension strand to a second branched primer, said primer comprising a front and a back module, each of said modules comprising a stem segment complementary to a stem segment in the other module, said modules annealing to each other via said stem segments, wherein each of said modules also comprises an arm segment which is complementary to a site in the template, the two sites being sufficiently close to each other in the template so that said branched primer annealed to the template forms a 3-way junction;

d. extending the arm of the front module of the second branched primer on the first initial extension strand by a polymerase enzyme to form a second initial extension strand which strand includes a complement to the front module of the first branched primer; and e. amplifying by PCR the second initial extension strand that contains the sequences of the stems of the first and the second branched primers, using amplification primers homologous to the stem sequences.

The stems of the first and second branched primers may have different sequences. Optionally, at least some of the amplification primers are protruding which means that when annealed to their priming sites, they cover one or more extra bases in these sites as compared to the front module. The extra bases are intended to increase the sequence-specificity of amplification.

An aspect of the invention is a method for amplifying a segment of a nucleic acid template by a polymerase chain reaction, said method comprising the following steps:

a. annealing the segment to a first covered primer comprising a first primer and a cover oligonucleotide. The primer and the cover oligonucleotides each have a stem segment that is complementary to the stem segment of the other; the primer and cover oligonucleotides are capable of annealing to each other via said stem segments; the first primer also comprises an arm segment which is complementary to a site in the template;

b. extending the arm of the first primer on the template by a polymerase enzyme to form a first initial extension strand;

c. annealing the first initial extension strand to a reverse primer, wherein the primer is extended on the first initial extension strand by a polymerase enzyme to form a second initial extension strand which includes a complement to the first primer;

d. amplifying the second initial extension strand by means of PCR using amplification primers that include the reverse primer and a primer homologous to the stem sequence of the first covered primer. The arm may contain an artificial base-position. An "artificial" base or nucleotide (e.g. inosine or 3-nitropyrrole) matches more than one of the 4 natural bases (A, C, G, T) in the opposite strand with approximately equal stability. At least one of the amplification primers is optionally protruding by one or more bases immediately downstream of the 3'-end. This protrusion increases the sequence-specificity of the amplification. The protruding amplification primers may include artificial bases. This reduces the number of possible sequences of these primers that need to be made.

The binding sites for different oligonucleotide modules are sufficiently close to each other in the template strand to enable the oligonucleotides to be in contact with one another while annealed to these binding sites. This contact should not be achieved by means that are too bulky such as avidin and biotin that restrict the functioning of the polymerase enzyme. In other words the binding should not present a physical obstacle for the polymerase function, but rather should permit the polymerase to perform the primer extension reaction. This contact essentially serves as a link between the modular oligonucleotides for enhancing the sequence specificity of priming by the modular primer, as compared to the sequence specificity of priming by one of the oligonucleotides alone.

The present invention also includes a library, that is, a collection of modular oligonucleotides in separate receptacles (e.g. microtubes), in which collection the base sequences of the oligonucleotides, e.g. front and back modules, proofreading primers, universal primers and the like. Oligonucleotides may have both constant and variable segments. The base sequence of the variable segment is generally shorter than seven nucleotides and varies from one oligonucleotide to another within the collection. The collection contains at least two percent of all possible sequences of the variable segment and at least five different sequences. This collection (library) of oligonucleotides is suitable for non-covalently forming a modular primer as described in this invention.

The present invention also includes a collection of modular oligonucleotides possessing a modification of a natural DNA conformation, which modification inhibits enzymatic primer extension of the 3'-end of the oligonucleotides. This collection can be used for making a modular primer of the present invention and for priming a strand extension reaction by the modular primer.

The present invention also includes a set (combination) of a first and a second collection of modular oligonucleotides, wherein all base sequences of oligonucleotides in the first collection comprise a variable segment and a first common segment, all base sequences of oligonucleotides in the second collection comprise a variable segment and a second common segment, the first and second variable segments sequences vary from one oligonucleotide to another within each of the two collections;

the first common segment of the first collection is complementary to the second common segment of the second collection and can bind non-covalently an oligonucleotide from the first collection to an oligonucleotide from the second collection, when the complementary segments are annealed to each other.

The following terms used elsewhere are equivalent to those used herein:

priming oligonucleotide=front module auxiliary oligonucleotide=back module composite primer=modular priming=front auxiliary=back holding segment=stem segment of the front module supporting segment=stem segment of the back module binding segment=arm binding site=part of the priming site complementary to an arm an "artificial" base or nucleotide (e.g. inosite or 3-nitropyrrole) matches more than one of the 4 natural bases (A, C, G, T) in the opposite strand with approximately equal stability.

Still further objects and advantages will become apparent from a consideration of the ensuing description and drawings.

Figure 1:
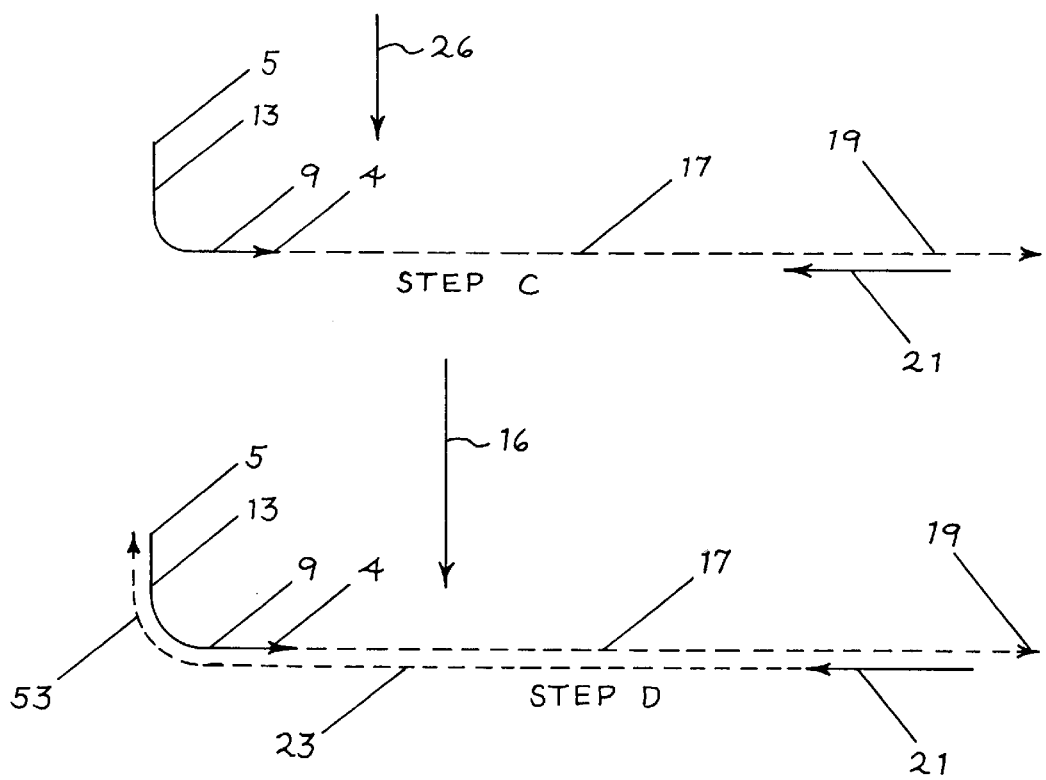
FIG. 1 is a flowchart of schematic representations of the PCR process where one initial primer is branched and the other is a conventional primer.

Step A. The first initial primer (branched primer) 1 is formed by a front module 2 and a back module 3 and is annealed to the template 15.

Step B. The primer is extended by a polymerase 14 along the template generating the first extended strand 17.

Step C. Then upon denaturation a conventional reverse primer 21 is annealed to the first extended strand.

Step D. The reverse primer is extended by the polymerase generating the second extended strand 23. This extension creates a priming site 53 for the front module of the first initial (branched) primer at the 3' end of the second extended strand. PCR is performed using the reverse primer and the front module of the first initial (branched) primer as amplification primers.

Figure 2:
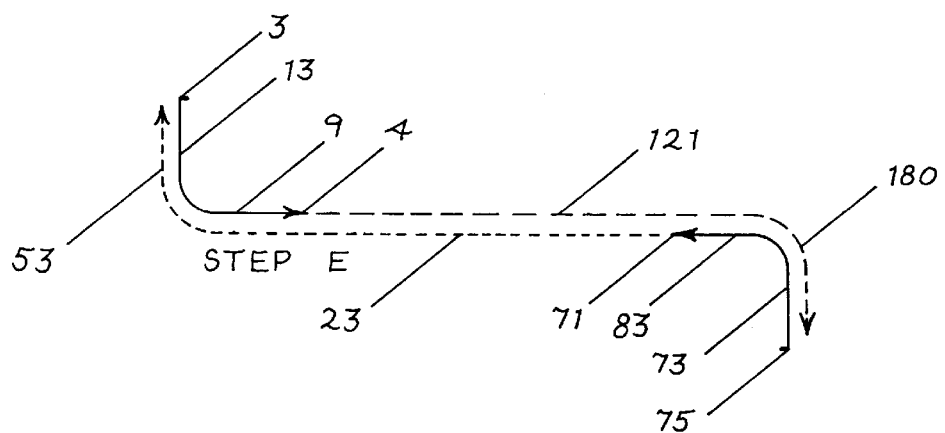
Figure 2:
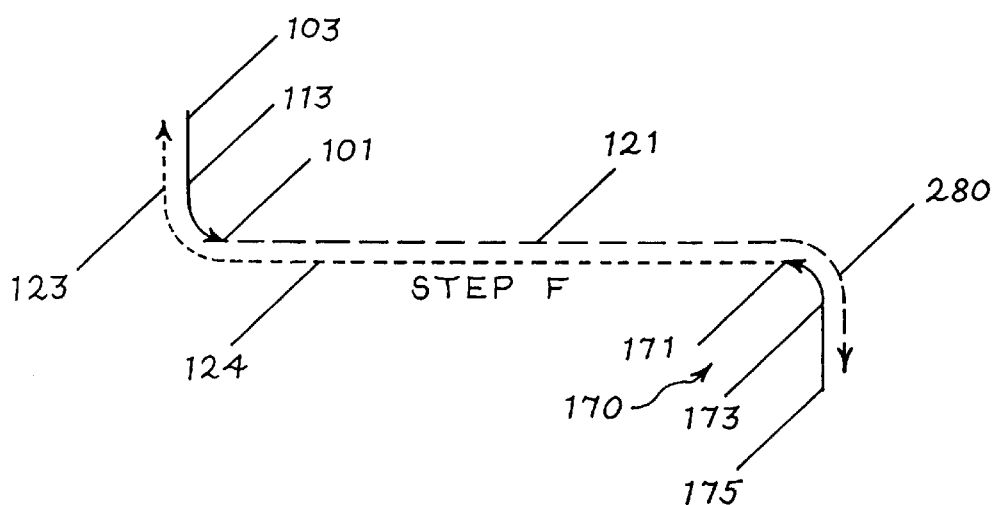

FIG. 2 is a flowchart of schematic representations of PCR where both initial primers are branched.

Step A The first initial primer (branched primer#1) 1 is annealed to the template 15.

Step B. The primer is extended by a polymerase 20 along the template 15 generating the first extended strand 17.

Step C. Upon denaturation a second initial primer (branched primer#2) 23 is annealed to the first extended strand 17.

Step D. The second initial primer is extended by the polymerase generating the second extended strand 23. This extension creates a priming site 53 for the front module 2 of the first initial (branched) primer 1 at the 3' end of the second extended strand.

Step E. PCR is then performed using the front module of the first initial primer (branched primer#1) and front module 71 of the second initial primer 70 (branched primer#2) as amplification primers. This is possible because the third extension generates the third extended strand 121 which contains at its 3' end a priming site 180 for the front module of the second initial primer (branched primer#2).

Step F. Optionally the PCR can be performed using stem-like universal primers (which are essentially homologous to the stem sequences) for the two front modules (of the first and second initial branched primers). The fourth extended strand 124 is generated.

Figure 3:

FIG. 3. shows expanded views of schematical examples of:

A. A front module 71 used in the PCR following the initial extensions. The front module is shown here priming on the second extended strand (or its own PCR product in any of the PCR cycles). The 4-th base from the 3'-end, T, is fixed (constant) in the front module library in order to reduce its size. The priming site shown here is created with the emergence of the second extended strand. This priming site does not exist in the original template; 33 shows cytosines incorporated by the polymerase opposite inosines of the front module;.

B. A PR1 primer (proof-reading primer 1) 27 used in the PCR following the initial extension. The PR1 primer is shown here priming on the second extended strand at the intended site while discriminating against alternative sites where its two "protruding" 3' end bases 25 are unlikely to match. "Protruding" means that extra bases complementary to the corresponding template bases at the intended priming site immediately downstream of the 3'-end of the PR1. The priming site shown here is created with the emergence of the second extended strand. This priming site does not exist in the original template. The 3' last 3 bases in this type of PR1 vary in the library of $4^3$=64 samples of PR1. The fifth base from the 3' end, T, is fixed (constant).

C. A PR2 primer (proof-reading primer 2) 29 used in the PCR following the extension with PR1. The PR2 primer is shown here priming on the sixth extended strand after PR1 has primed on the 4-th extended strand. The priming site shown here is the complement of tne extension of PR1. This priming site does not exist either in the original template or in the second extended strand. The PR2 primer primes at the intended site while discriminating against alternative sites where its two 3' end bases 25 are unlikely to match. The eighth base from the 3' end, T, is fixed (constant) while the last 3 bases at the 3'-end of this structure of PR2 are variable in the library of $4^3=64$ PR2 sequences. 38 shows cytosines incorporated opposite inosines of the PR1.

Figure 4:
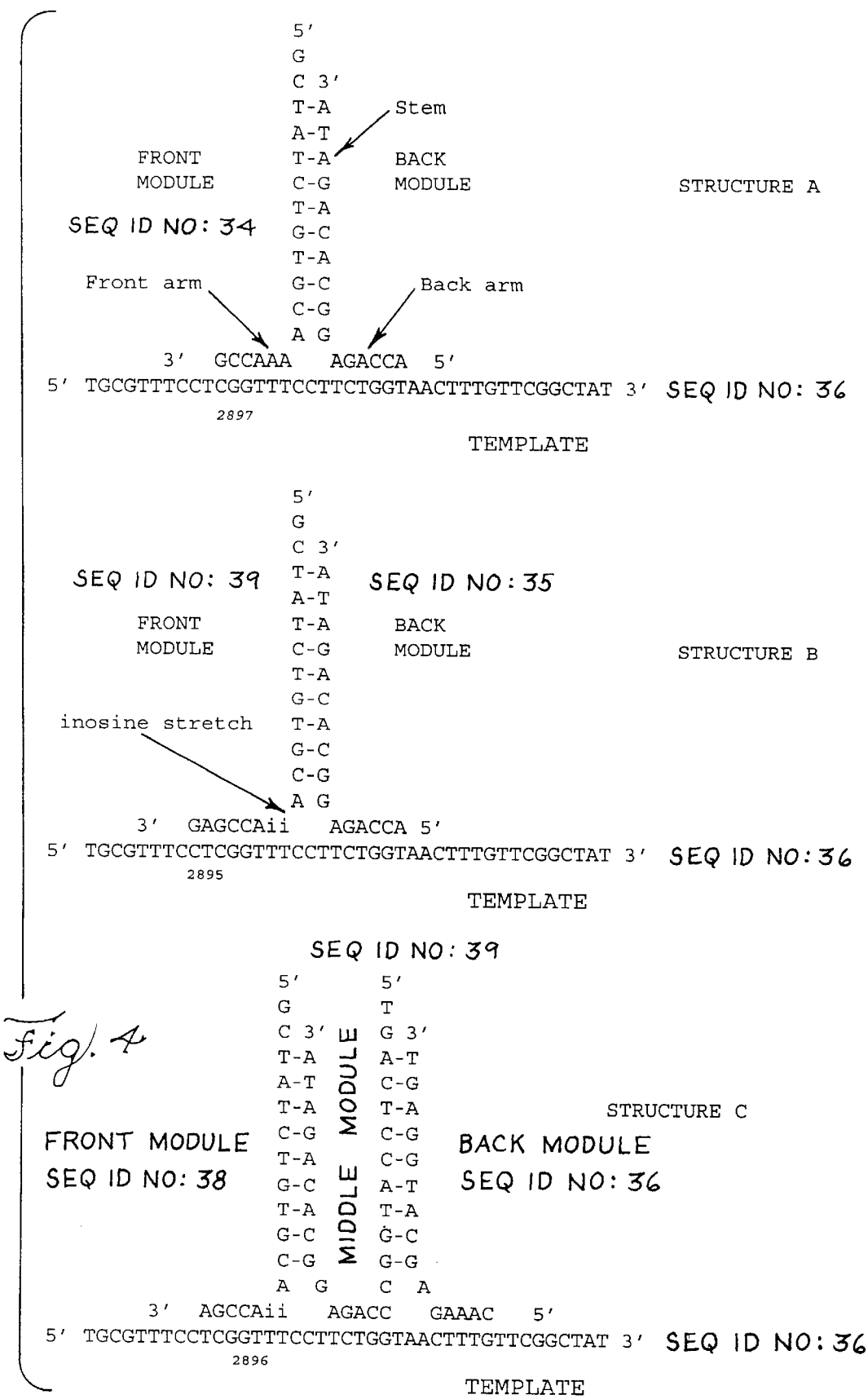

FIG. 4. presents illustrations of branched primer structures:

Structure A. The simplest branched primer structure, consisting of two modules (marked "front" and "back") annealed to each other via the "stem" duplex. Each of the two modules has an "arm" annealed to the template;

Structure B. A branched primer of a structure similar to A, except that a stretch of two inosines is inserted at the 5'-end of the front arm in order to alleviate steric hindrance that the 3-way junction may present to the polymerase;

Structure C. A branched primer consisting of three modules annealed to one another via two stems. This structure has a longer total length annealing to the template and optionally has a shorter variable portion in each arm.

Figure 5:
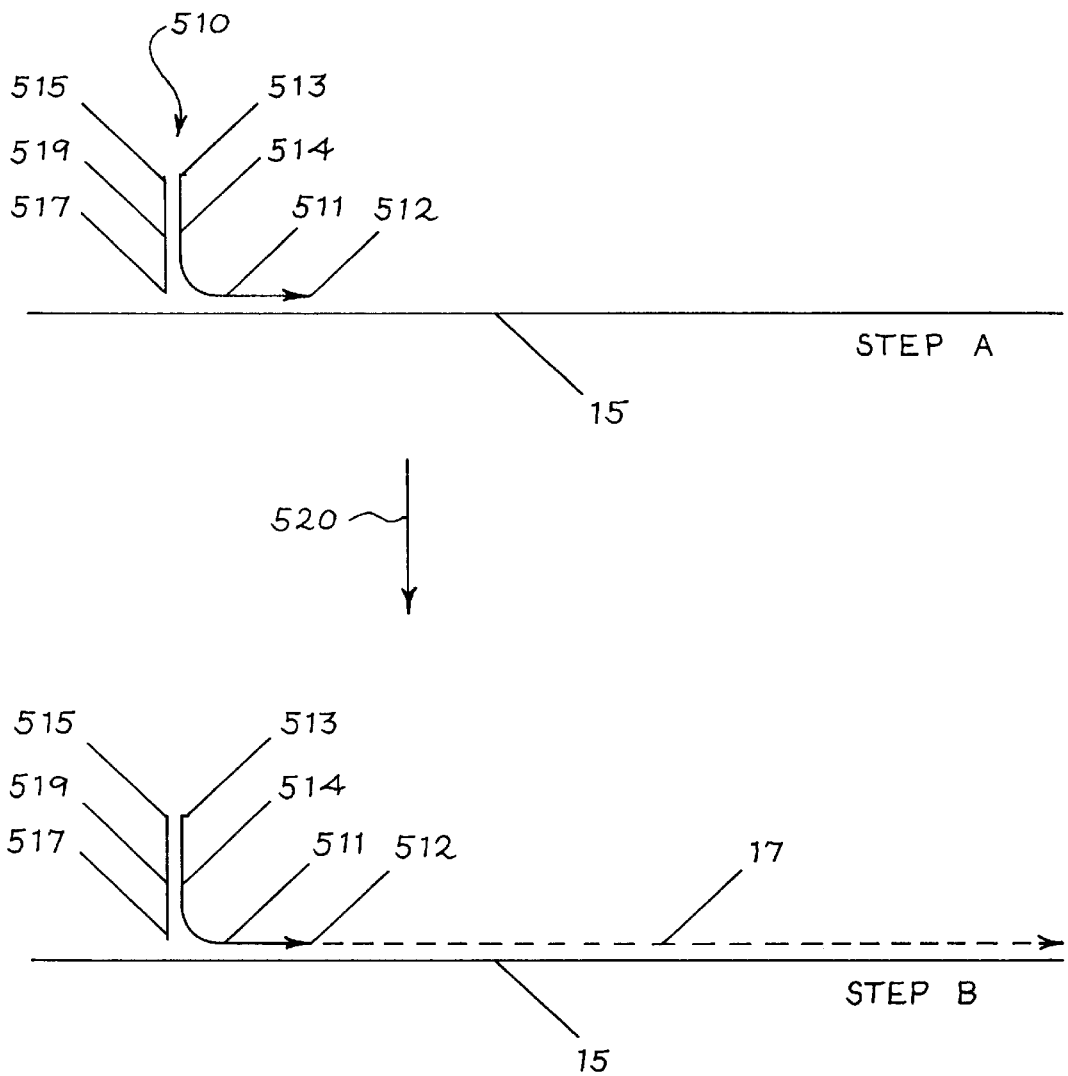

FIG. 5. is a schematic drawing of a covered primer in the initial extension:

Covered primer 510 is a primer which contains a double stranded portion near its 5' end 513 and a single stranded portion near its 3' end 512. In other words it can be viewed as a branched primer without the arm of the back module.

Step A. The first initial primer (covered primer) 510 is annealed to the template 15.

Step B. The primer is extended by a polymerase along the template generating the first extended strand. Subsequent PCR is performed similar to FIGS. 1 and 2. The cover oligonucleotide has only one sequence (stem) and thus requires no library (unlike the back module).

Notations in the Figures:
1. first initial (branched) primer.
2. front module.
3. back module.
4. 3'-end of the front module.
5. 5'-end of the front module.
6. 3'-end of the back module.
7. 5'-end of the back module.
9. arm of the front module.
11. arm of the back module.
13. stem.
14. extension by a polymerase.
15. template.
16. extension with polymerase creating a priming site for the front module #1.
17. first extended strand.
18. primer for the reverse strand can be another branched primer; denature and anneal with branched primer #2 for the reverse strand.
19. 5'-and of the first extended strand.
20. extension by a polymerase.
21. conventional (long) reverse primer.
23. second extended strand.
25. proof-reading (discriminating) bases (shown in lower case).
26. denature and anneal with reverse primer.
27. first proof-reading primer (PR1) also termed first homing primer.
29. second proof-reading primer (PR2) also termed second homing primer.
31. fourth extended strand.
33. cytosines incorporated by the polymerase opposite inosines of the front module.
38. cytosines incorporated opposite to inosines of the PR1.
41. sixth extended strand.
53. newly created priming site for the front module of the first branched primer.
70. second initial primer.
71. front module of the second initial branched primer.
72. 3'-end of the front module of the second initial branched primer.
73. stem of the second initial branched primer.
75. 5'-end of the front module of the second initial branched primer.
77. 3'-end of the back module of the second initial branched primer.
79. arm of the back module of the second initial branched primer.
81. 5'-end of the back module of the second initial branched primer.
83. arm of the front module of the second initial branched primer.
101. 3'-end of the universal stem-like primer for the first branched primer.
103. 5'-end of the universal stem-like primer for the first branched primer.
113. universal stem-like primer for the first branched primer.
121. third extended strand.
123. newly created priming site for the universal stem-like primer for the first branched primer.
124. fourth extended strand.
170. universal stem-like primer.
171. 3'-end of the universal stem-like primer for the second branched primer.
175. 5'-end of the universal stem-like primer for the second branched primer.
173. universal stem-like primer for the second branched primer.
180. newly created priming site for the front module of the second branched primer.
280. newly created priming site for the universal stem-like primer of the first branched primer.
510. covered primer.
511. arm of the covered primer.
512. 3'-end of the covered primer.
513. 5'-end of the covered primer.
514. stem.
515. 3'-end of the cover.
517. 5'-end of the cover.
519. cover.
520. extension with polymerase and dNTPs.

DESCRIPTION OF THE PREFERRED EMBODIMENTS

The present invention provides compositions for primers used in methods for amplifying a nucleic acid segment, e.g. by the polymerase chain reaction (PCR). Limitations of current methods are removed. Compositions of the present invention include branched modular primers and covered primers.

The impending automation of assembling large numbers of different PCR reactions will be greatly facilitated by the invention which allows a primer of any sequence to be instantly assembled using a pre-synthesized oligonucleotide library skipping the step of custom primer synthesis.

Branched and Covered Primers

A distinctly different mechanism of modular primer action of the present invention involves novel structures designated "branched" modular primers (FIGS. 1, 2, 4). In a branched primer the modules are physically linked together, that is they hybridize to each other as well as to the target DNA, thereby forming a 3-way junction (FIG. 4). The specificity of branched primers is due to cooperative annealing of the modules to the template at the intended site, a mechanism different from that of contiguous modular primers described in Beskin et al (1995).

The branched primer structure requires two libraries respectively designated hereinafter as consisting of either "front" or ubackw modules of different oligonucleotide sequences. "Front" is used herein to refer to the 3' extending (downstream) end and "back" to the 5' non-extending end (upstream), both relative to the direction of the extension of the nucleic acid sequence by the polymerase (FIGS. 1, 2). Each oligonucleotide is generally stored in a separate receptacle e.g. microtubes. Different front modules generally include the same constant sequence complementary to the corresponding constant sequence in the back modules. In assembling a branched primer, the two constant segments anneal to each other, forming a double-stranded handle (marked stem in FIG. 1A and in FIG. 4A). In contrast, the variable sequences (marked "arm" in FIG. 1A and in FIG. 4A) vary from module to module in each of the two libraries.

Initial priming for a PCR reaction is performed by a "first initial primer" being extended at the intended site on the template. The first initial primer can be a "branched modular primer" (FIGS. 1 and 2) or a "covered primer" (FIG. 5). FIG. 5. presents a covered primer in the initial extension: Covered primer is a primer which contains a double stranded portion near its 5' end and a single stranded portion near its 3' end. In other words it can be viewed as a branched primer without the arm of the back module. The cover oligonucleotide has only one sequence (stem) and thus requires no library (unlike the back module).

The strand resulting from the extension of the first initial primer is called the "first extended strand" (FIGS. 1, 2, 5). If the opposite strand (reverse) primer is a conventional primer (that is a type of primer used in the art that is not branched and not modular), the first extended strand is then used as a template for PCR amplification (FIG. 1). In this type of amplification, the two PCR primers are a) the conventional reverse primer and b) the front module of the first initial primer (or a universal primer homologous to the stem of the front module). In the first cycle of PCR, the reverse primer primes on the first extended strand and gets extended all the way till the 5'-end of the front module of the first initial primer (FIG. 1D). This extension creates a priming site for (is complementary to) the front module of the first initial primer (or stem-like universal primer, that is a primer homologous to the stem portion of the front module). This priming site does not exist in the template until this point in the process (FIG. 1D).

Instead of being the conventional primer, the reverse primer can be another branched modular primer or a covered primer (FIG. 2C). In this case the first extended strand (upon denaturation) is primed upon (i.e. is used as a template) in the reverse direction by a second initial primer (a branched modular primer or a covered primer) (FIGS. 2C, D). The second initial primer is extended on the first extended strand (FIG. 2D). The second initial primer gets extended all the way till the 5'-end of the first extended strand (the extended front module of the first initial primer) as the conventional reverse primer does in the example above. The strand resulting from the extension of the second initial primer is called the second extended strand (FIG. 2D). This extension creates a priming site for (complementary to) the front module of the first initial primer or for the second stem-like universal primer (FIG. 2D). This priming site does not exist until this point in the process.

PCR amplification is performed using the front modules of the two initial primers (first and second) (FIG. 2E) or two universal (stem-like) primers, homologous to the two stems (first and second) (FIG. 2F) as PCR amplification primers. In the first PCR cycle, the first amplification primer (front module or universal primer) primes at its newly created priming site on the second extended strand. It gets extended all the way till the 5'-end of the second extended strand (the extended front module of the second initial primer).

This extension (in the first cycle of the PCR) creates a priming (complementary) site for the front module of the second initial primer (or for the second universal primer) which module is used as the second PCR amplification primer. This priming site does not exist until this point in the process. Now, from the second PCR cycle onwards, both amplification primers (forward and reverse) have their priming sites at the opposite ends of the intended PCR fragment product and the exponential PCR-amplification proceeds using thermocycling. Note that in this amplification, both PCR primers (e.g., front modules of the first and the second initial primers) are functioning as conventional primers, and are not functioning as branched modular primers or their parts, as they were in the two initial extensions.

The PCR amplification can be performed in at least two ways:

1) using an aliquot of initial extensions as templates and
2) without aliquoting, that is amplifying in the same tube where the initial extension has been performed.

In (2) much lower concentrations of initial extension primers may be required as compared to those in (1) and to those of amplification primers which are added after the initial extension.

"Proof-Reading" Primers

To improve the priming specificity, the PCR amplification primers can be designed to perform what is termed herein "proofreading" a procedure intended to suppress possible PCR products arising from mispriming by the first and/or the second initial primers. The proof-reading starts with a set of two (forward and reverse) "first proof-reading primers" (PR1). These (PR1s) are similar in terms of some of their sequence to the front modules of the initial primers of steps 1 and 2, (these front modules are described above for use in PCR amplification) but each has one or more extra nucleotides protruding beyond the 3'-end of the initial primer (as measured by the template coverage) (FIG. 3B). The purpose of the protruding nucleotides is to match the intended priming site while discriminating against possible alternative priming sites in the template where the first or/and the second initial primers could misprime. The discrimination occurs due to mismatches between the (protruding) bases near the 3'-end of the primer and the template bases at the alternative sites. The occurrence of the full match at an alternative site is statistically unlikely: $1/16$ for 2 protruding bases in each primer, i.e. $1/16 \times 1/16 = 1/256$ for matching both (forward and reverse) primers in a random sequence. Thus the proof-reading primers serve to increase the PCR specificity which is now determined not only by the arm sequences of the initial-primers, but also by the protruding bases in the proof-reading primer.

The first proof-reading primers (PR1s) have artificial bases such as inosines (or other types of artificial, nondiscriminating bases). The presence of inosines in the first proof-reading primers in positions where sequence-specific bases were in the arm of the initial primer makes the proof-reading primers "universal". The term "universal" implies that the same proof-reading primer matches a great number of the sequences of the initial primers. Thus the number of possible different proof-reading primers may be as small as the number of possible different proof-reading (protruding) base-combinations multiplied by the number of different stems (typically two). The number of different possible proof-reading (protruding) base-combinations is $4=4^1$ base-combinations for one protruding base, $16=4^2$ base-combinations for two protruding bases and $64=4^3$ base-combinations for three protruding bases. Apart from the protruding bases, proof-reading primers may contain additional variable bases. For example in FIG. 3B the PR1 primer contains one additional variable base adjacent to the 2 protruding bases. initial and proof-reading primers together form a library of oligonucleotides that can serve a great variety of priming sites.

The proof-reading primers have some similarities to primers described in U.S. Pat. No. 5,487,985 in column 5, for use in AP-PCR. However, proof-reading primers combined with the initial primers prime site-specifically, while the AP-PCR primers work as arbitrary primers. Instead of being custom made (as the AP-PCR primers are) because they have to match the full long sequence of the initial primer) the proof-reading primers are selected from a library of very few universal primers. What makes their number small is that much of the proof-reading primer sequence (a 5'-portion) matches the stem sequence of the initial, branched (or covered) primers, which is constant, the same for all primers and all priming sites. Much of the arm sequence, which is variable in the initial primer, becomes largely constant (replaced by artificial bases) in the proof-reading primers.

The amplification with the first proof-reading primers of the previous step (PR1s) is optionally followed by (or combined with) a second round of amplification (FIG. 3C), with a set of two second proof-reading primers (PR2). The second proof-reading primers have one or more bases "protruding" beyond the 3'-end of the PR1s (FIG. 3C). The purpose of the extra protruding nucleotides is to further discriminate against possible alternative sites (where mispriming could occur in the initial extension) while matching the intended priming site. The discrimination occurs due to mismatches between the protruding bases, near the 3'-end of the primer and the template bases at the alternative sites. The second proof-reading primers (PR2) have (FIG. 3C) in the stretch corresponding to the inosines (or other types of artificial bases) of the first proof-reading primers (PR1). The PR2 primers have inosines (or other types of artificial bases) in the stretch corresponding to at least some of the protruding bases of the first proof-reading primers. (FIG. 3C) Both (Gs) and inosine are part of the constant sequence (do not vary throughout the PR2 library) which makes the PR2s universal. As in the case of the first proof-reading primers the library size of the second proof-reading primers can be kept small because of these constant positions. An additional purpose of the artificial bases in PR1 and PR2 is to enhance the discrimination of the primers. Artificial bases (non-discriminating, universal were reported to enhance discrimination (Guo, 1997). To achieve high discrimination stringent PCR conditions are essential.

Further proof-readings (third, fourth, nth, termed PR3, PR4, PRn) may be added. The proof-reading reactions (PCR-amplifications) with PR1, PR2, PR3, PRn are performed as: either (A) a series of reactions or (B) combined in one reaction (single-tube reaction). In the case of A (a series of reactions), an aliquot of the PCR products amplified with PR1s is taken and amplified with PR2, and an aliquot of those products is then amplified with PR3, and so forth. In the case of B (single-tube reaction), the sets of PR1, PR2, PR3, and so forth primers are combined in one reaction (e.g., in a single receptacle). Because of the Gs replacing inosines in successive PR pairs, each pair of PR primers starts priming only after the previous pair has primed twice (to make a complementary copy of itself where the polymerase incorporates C opposite each inosine). It is only at this point that the correct priming site would exist. The pair of PR primers being the last to prime is then used to produce the intended product. The following precautions (a and b) can be taken to ensure that the last PR pair out-competes the other PRs in terms of its amplification efficiency:

a. the last set (nth) of proof-reading primers (PRn) is added in several-fold higher concentration than the preceding PR sets;

b. the last PR set has either a mismatched 1–4 base long tail or one or more internal mismatches (bases sequence differences as compared to the last-but-one PR sequence). To compensate for these mismatches the length of the last PR is slightly increased (the tail may protrude beyond the end of the opposite strand). The purpose of the increase in length is to make. its Tm (melting temperature) in its priming with these mismatches (in the first cycles it can prime) close to the Tm of the other PRs in the reaction. However the Tm of its subsequent priming cycles is a few degrees higher, as the mismatches become fully matched (since after the second cycle onwards, the PCR primer has its priming site being a complementary copy of itself). In the PCR cycle temperature regime, that Ta (annealing step temperature) is then chosen high enough to ensure a high stringency (hence low efficiency) of priming by the last PRs (when mismatched) and by the other PRs. Therefore, this choice of Ta ensures a high stringency of annealing (and thus specificity of priming) for all PRs except for the last PR in the later cycles (when the last PR is fully matched). The reason for the difference is that after its first priming and the synthesis of its exact complementary copy, the last PR has a much higher priming efficiency as it becomes fully matched.

The discrimination against alternative priming sites (proof-reading) occurs during the first priming only when the mismatches whether in the stem portion or near the 3'-end still exist. Therefore, maintaining higher stringency for the proof-reading purposes is not required in the subsequent cycles of the last PR and the disappearance of the intentional mismatches should cause no loss of specificity.

If the presence of inosines close to the 3'-end of the PR primers weakens PCR amplification too much, then in addition to the last PR (designed and used then without precautions a and b above) a 'final' primer set is added for amplification in the PCR. The final primer is similar to the last PR except that all or some of the inosines are replaced with guanines (Gs) (accordingly, the final primer's length is adjusted to correct the melting temperature). Precautions a and b mentioned above are then applied to the final primer, or pair of primers instead of applying them to the last PR. The use of universal primers in PCR is advantageous because they have known optimized annealing step temperature and other PCR conditions.

Strand Displacement Amplification with Branched Primers

Branched primers can be applied to the type of PCR amplification known as SDA–Strand Displacement Amplification (Walker et al. (1992, 1993) The stem (and accordingly the PR) sequence has then to include an appropriate restriction site. The two initial extensions can be done as described herein with a denaturation step between them. The amplification can then proceed as in SDA with no need for thermocycling (one of the main advantages of SDA).

Branched Primer Structure, Assembly And Specificity.

To design a branched primer for a particular site in the template, the arm sequences of the two modules (front and back) are selected to match adjacent sequences in the DNA or RNA template at the intended priming site (FIG. 4). Aliquots of the two selected oligonucleotides (from the front and back module libraries respectively) are then mixed for the annealing and sequencing reactions.

Use of Base Modifications The back module or its arm, or the front module may include base modifications to improve performance. Modifications of either bases or backbones in modular primer that improve the stability of annealing, include (1) PNA, (2) methyl phosphonate, (3) 5-methylcytidine and (4) 2-aminoadenosine (Azhikina et al., 1993; Nielsen et al., 1991; Egholm et al. 1993).

Inosine Stretch Length Optimization.

In view of possible steric hindrance to the polymerase by the 3-way junction, it is preferable to increase the front module's arm length without enlarging the library of first modules. For this purpose a stretch of inosine bases was inserted in the front module between the six specific bases of the arm and the junction point, as shown in FIG. 4B. Inosine is known to have little discrimination between the four natural bases in the opposite strand, and although it functions as an artificial base, it does not contribute as much to the stability of the double helix as the 4 natural bases do. (Ohtsuka et al. 1985)

The back module is normally used in excess over the front module, because otherwise the front module unattached to the back one may randomly misprime. Indeed, if the molar concentration of the front module exceeds that of the back one, the priming becomes less specific.

In some cases, random mispriming by the stem segment of the back module needs to be prevented. This may be achieved by chemical modification of the 3'-end of the second module during oligonucleotide synthesis, so that the modified 3'-end is protected from being extended by the polymerase. Of a number of such 3'-end modifications possible with contiguous modular primers, 3'-phosphate propyl ester is preferred (Glen Research, Sterling, Va., cat. #20-2913-10).

Variations In Branched Primer Structure.

The number of unpaired bases in the template was varied between the two arms. The optimal number was found to be 2 bases. Interestingly, this is also the minimal number needed to stabilize DNA 3-way junctions as measured by UV melting and competitive gel electrophoresis. (Leontis et al., 1991). In practice, the number of unpaired bases may need to be many more than 2. In a separate experiment, the number of unpaired bases between the arm and the stem was varied; the optimum was found to be one unpaired base in each of the two modules. Various stem lengths were tested from 8 to 25 bases. Most stem lengths did work, and no reproducible optimum was found.

In order to strengthen priming by branched primers without increasing the variable region length (and hence library size), degenerate positions were inserted into the arms. The insertions were made at the 5'-end of either the back or front arm, or both. In general, the more degenerate bases added, the stronger the priming signal became, and the effect was in some cases quite dramatic. This stronger priming was probably due to an increase in the affinity of the primer for the template, caused by the longer arms. It remains to be seen whether degenerate base positions may adversely affect the specificity of priming, and if so, whether the specificity may be temperature dependent.

The number of different oligonucleotides in each of the two libraries depends on the length of the variable segment in the arm. For example, the complete library of all possible sequences of a pentamer would consist of 1,024 oligonucleotides. Each additional base in the variable segment increases the size of the library 4 fold. However even a partial library may suffice for the purpose of assembling primers, in view of the freedom to shift the priming site within a reasonable span of the template sequence, usually ranging over a hundred bases or longer.

The number of modules in a branched primer does not have to be limited to two. FIG. 4C shows a branched primer structure consisting of three modules annealed to one another (via two stems) which was also found to work. One advantage of such a structure over the two-module branched primers discussed above is the greater combined arm length annealed to the template. The greater annealing length may translate into a higher stability or strength of the primer, a better ability to compete with the secondary structure of the template, and perhaps also into a higher sequence-specificity of priming. On the other hand, the above advantages can allow shorter arms. For example, a pentamer rather than a hexamer variable region was tried in the three-module branched primer and found to work. Having the variable, region shorter by one base would result in a 4-fold reduction in the library size of each of the three modules (first, second, third).

Oligonucleotide Libraries

An oligonucleotide library is a collection of samples in separate receptacles e.g. microtubes, each sample containing oligonucleotides of a specific sequence. A front module and a back module are chosen from their respective libraries. First, an annealing site is selected within a known region of template strand. Then, the sequences of front module arm and back module arm are selected to be complementary to the sequences of closely spaced binding sites. Within each library, the sequences of the oligonucleotides change from sample to sample, giving a choice of a large variety of sequences. The two binding sites together should be long enough to make the selected annealing site sufficiently unique within the entire template strand.

Sequence Specificity of Priming

When used alone, the front module may possess more than one priming site in the template, where it can anneal and serve as a primer.

Much more sequence specific priming occurs when the front module is used together with the back module, than when it is used alone. The increased sequence specificity means that stronger priming occurs at the selected priming binding site, where the two arms match the template as compared to other possible priming sites in the template, where the two arms combined they are likely to be less matched to the template. For a more general design of a modular primer which may consist not of just two, but of, generally speaking, two or more oligonucleotides, the sequence specificity has a similar property.

Sizes of Libraries of Modular Primers

Two 6-mer arm libraries can be, for example, the following structure. The priming library of the arm sequences has the structure 5'-A-X-X-X-X-X-3'. It means that, of the six nucleotides, one, sitting on the 5' end, is fixed. In this example it is adenine. This 5'-terminal position has the same base in all the samples of the priming library. The other five positions form a variable segment, that is a segment in the modular oligonucleotide, whose base sequence varies from sample to sample. Each of these five positions, shown as X, is a variable position, which means that this base may change from sample to sample within the library, being either A, C, G, or T, depending on the sample sequence. Different combinations of bases in the variable positions can form all possible sequences of the 5-mer X-X-X-X-X variable segment, $4^5$=1,024 possible combinations, within the 6-mer 5'-A-X-X-X-X-X-3'.

The absence of variability in the 5'-terminal position, which has A-base in all samples of this example, is introduced in order to reduce the number of samples in the library by a factor of 4. The reduction is from $4^6$=4,096 samples in a complete 6-mer library of the 5'-X-X-X-X-X-X-3' structure, down to $4^5$=1,024 samples in the reduced library of the 5'-A-X-X-X-X-X-3' structure adopted in this example. The price paid for that reduction is the loss of about ¾ of all possible 6-mer binding sites in a random template sequence. After such 4-fold reduction a whole quarter of all 6-mer binding sites still remains in a random template. Thus, on the average, every fourth base in a random sequence template is T and can be the 3'-end base of a 6-mer binding site for a priming library. This should be more than sufficient to select a single 6-mer priming binding site within a known sequence stretch, usually at least dozens bases long. its preferable to avoid annealing sites involved in stable secondary structures of the template, such as hairpins. Computer programs are available for estimating the secondary structure potential of a given sequence.

The following example demonstrates another possible way to reduce the size of an oligonucleotide library. In this example, the second library has the oligonucleotide structure of 5'-N-X-X-X-X-X-3'. Here, N denotes a degenerate position at the 5'-terminus of the 6-mer long oligonucleotide. A degenerate position is one which can be filled by any one of the four natural bases, A, C, G, or T. One way to fill a degenerate position is to use a mixture of some or all of the four bases in the synthesis of this position in the oligonucleotide. Another way is to mix non-degenerate oligonucleotides differing in this base, after their synthesis. In this example, the 5' terminal nucleotide has all four possible bases mixed in equal proportions in each sample of the library. The other five positions, shown as X-X-X-X-X, form a variable stretch within the back module. They can have either A, C, G, or T base, but not mixed in a single sample, in each of the five variable positions of the oligonucleotide 5'-N-X-X-X-X-X-3'.

Therefore, although both front and back arm libraries consist of 6-mer oligonucleotides, only 5 out of the 6 positions are variable from sample to sample. All possible sequences of the five variable positions, X-X-X-X-X, can form $4^5$=1024 sequence samples in each of the two libraries. If either of the two libraries were complete, that is contained all possible sequences of the annealed length, six bases long, it would consist of (contain) $4^6$=4,096 sequence samples. In practice though, libraries do not have to be complete. Some of the sequences may or should be absent from the libraries. For example, a sequence containing a CGCG stretch may be chosen not to be represented in a library because of its rare occurrence in genomes. Or, a particular sequence may happen to have a lower efficiency than others as a component of the modular primer and be excluded from a library for that reason. Or, some sequences may inhibit a DNA polymerase activity as a result of sequence dependent curvature of the double-stranded DNA (Ulanovsky et al., 1987). Or, some sequences may be excluded from a library just in order to reduce the size of the library. For example, the above structure 5'-A-X-X-X-X-X-3' of the front module library can be viewed as exclusion of all 6-mer sequences starting from C, G or T base from a complete library of all possible 6-mers 5'-X-X-X-X-X-X-3'. The purpose of that particular exclusion is, as mentioned above, to reduce the library size to ¼ of the complete library size. The reduction of the library size can also be achieved by imposing a limit, either a minimum or a maximum, on the G+C content in the oligonucleotides, or by imposing another restriction or a combination of restrictions on the oligonucleotide sequences in the library.

Different schemes of reduction in library size can supplement each other. For example, the reduction by fixing the 5'-terminus position base, discussed above, can be followed by a further reduction in the library size by limiting the G+C content of the library sequences. However, reduction of a library to a too small size reduces the usefulness of the library for DNA sequencing purposes. Indeed, a library containing less than 2% of the all possible sequences of the variable segment can serve less than one in fifty possible binding sites for the particular modular oligonucleotide in a random sequence template. The portion of the sites the library can serve is even smaller, if the library structure contains a fixed base position, as in the priming library example above. Such a small size can make it difficult to select an annealing site for modular primer within a newly sequenced template stretch, which is often short. A library should also have a reasonable absolute size to be useful. It should contain at least five different sequence samples to be of practical use.

In FIGS. 4, A, B the binding sites for both front and back module arms are 6-mers (6 and 6 bases). In another embodiment, the corresponding lengths of the two binding sites can be 5 and 7 bases, such as 5'-A-X-X-X-X3' in front and 5'-N-N-N-X-X-X-X-3' in libraries. In different embodiments, the lengths of the front and back arms also can differ from the examples above, e.g. it can be 4 and 6; or 5 and 6; or 6 and 5 bases and other combinations. Generally, the sizes of the front and back arm libraries may be the same as, or different from the examples above.

Branched Modular Primer

FIG. 4 schematically shows an embodiment of a modular primer annealed to a template strand. The modular primer is kept together by annealing between its oligonucleotide modules. The modular primer comprises two oligonucleotides: the front module with its 3'-end and 5'-end, and the back module with its 3'-end and 5'-end. The front module comprises a stem segment of the front module complementary to stem segment of the back module in the back module. FIG. 4 shows stem segment of the front module annealed to stem segment of the back module. The front module further comprises an arm complementary to its binding site in a template strand. The back module comprises an arm complementary to its binding site in a template strand.

Oligonucleotide Libraries for Branched Modular Primers

In order to bind to the selected priming site, both the front module and the back module are chosen from their respective libraries. All the sequences in the first library contain the same sequence of stem segment of the front module. All the sequences in the second library contain the sequence of stem segment of the back module complementary to stem segment of the front module. Therefore, regardless of a particular choice of the two samples from the two libraries, the stem segment of the front module anneals to stem segment of the back module.

In contrast to the stem segments, arms vary within each library, their sequences changing from sample to sample. When a particular modular primer is being selected from the two libraries, arms are chosen to be complementary to binding sites in a known region of template strand. The two segments annealed to binding sites should be long enough to make the selected annealing site sufficiently unique within the entire template strand.

Unqueness of the Annealing Site

The selection of a annealing site involves choosing two close binding sites in the template: for a front and an back module. These oligonucleotides are then selected from their libraries to have their arm sequences complementary to their binding sites in the template.

A modular primer can have more than two oligonucleotides, for example three. The third oligonucleotide has a binding site in the template, close enough to the binding site of the back module, to contribute to the priming efficiency. Contact is maintained by annealing a part of the third oligonucleotide to an additional segment of the back module specially added to its 5'-end in the scheme of three oligonucleotide modular primer, as shown in FIG. 4. This additional segment of the back module has the same sequence in ail samples of the back module library, this sequence being complementary to a segment in all samples of the third oligonucleotide library.

If each of the three arms has no degenerate positions, the total unique primer-to-template annealing length is the sum of the three arms lengths. This greater annealing length enhances the priming efficiency by strengthening the binding of the modular primer to the template.

In the same manner, a modular primer structure can contain four or more oligonucleotides. Each additional oligonucleotide is connected with the preceding one by annealing of their complementary segments. The binding site for the additional oligonucleotide is selected in the template sufficiently close to that of the preceding oligonucleotide to maintain contact between the two oligonucleotides, while maintaining their annealing to the template.

Connecting (unpaired) Nucleotides in Modular Branched Primers

A nucleotide connecting the variable segment with the rest of the oligonucleotide (linkers) can have any base, but preferably such modification, as Inosine or Deoxynebularin (both available from Glen Research Corp., Virginia, USA), which have approximately equal energy of base-pairing with all four normal bases. This linker between the arm and stem can also be just a chain of atoms (linker) with no base at all, like "AminoModifier II", available for DNA synthesis from Clontech, Calif., USA. The purpose of the weak base-pairing of the linker is to make the annealing site more unique. Otherwise, that is if the linker has one of the four normal bases without weakened base-pairing, it can generate undesirable extra binding sites together with nucleotides adjacent to it.

In the example above, the connection between the variable segment and the rest of the oligonucleotide consists of one nucleotide. However, in other schemes it may consist of more than one, or no nucleotide at all. For example, for reasons of the polymerase activity or/and stability of the primer-template complex, tight base-stacking may be desirable between stems. This would require the absence of the linker nucleotide in the front module. On the other hand, the steric interaction of a particular polymerase with the double helix may require more than one artificial nondiscriminating nucleotide in the front module to keep its second stem further away.

The following are Detailed Examples of Particular Experiments of PCR Amplification (of Lambda Phage DNA fragments) Using Branched Primers.

Four branched primers, each consisting of a front module and a back module, were designed for priming sites in Lambda Phage DNA. Two branched primers were designed to prime in the forward direction, towards the sites of the reverse primers. The other two (reverse) primers in turn primed on the opposite strand so that they could be extended in the opposite (reverse) direction (towards the forward primers). The sites position numbers were: forward—19816 and 20397, reverse—19379 and 19654, where the numbering refers to the position of the 3' end of the front module (the numbering and the Lambda Phage sequence were as in the GenBank, Accession number X00906). The forward and reverse branched primers were designed to have different stem sequences. Control conventional primers were made complementary to each priming site, in the same orientations as the branched primers.

The oligonucleotide notations below: FM—front module, BM—back module, PR1 and PR2—"proofreading" amplification primers, LP—conventional long primer, Uni—universal stem-like primer. Bold type shows the arm bases of the front and back modules, and variable bases of the amplification primers. Upper case shows the bases in the priming site that are complementary to the arms of the branched primer. The sequences were as follows:

At site position number 19379 (reverse) in Lambda Phage:
Priming site 5'-tcttacGGTMTccattGTACTGccggaccac-3' SEQ ID NO:1
FM-379 5'-acg ggt acg acg ttc aii att acc-3' SEQ ID NO:2
BM-379 5'-ica gta cic gaa cgt cgt acc cg-3' SEQ ID NO:3
PR1-379 5'-tgt acg acg ttc agg iit iic gt-3' SEQ ID NO:4
PR2-379 5'-ctg acg ttc agg ggt ggi ita a-3' SEQ ID NO:5
LP-379 5'-gtg gtc cgg cag tac aat gg-3' SEQ ID NO:6
Uni (reverse) 5'-acg ggt acg acg ttc agg-3' SEQ ID NO:7
At site position number 19654 (reverse) in Lambda Phage:
Priming site 5'-tttactGCCATAttctcCCCACAaaaaagc-3' SEQ ID NO:8
FM-654 5'-acg ggt acg acg ttc aii tat ggc-3' SEQ ID NO:9
BM-654 5'-itg tgg gic gaa cgt cgt acc cg-3' SEQ ID NO:10
PR1-654 5'-tgt acg acg ttc agg iit iic ag-3' SEQ ID NO:11
PR2-654 5'-tag acg ttc agg ggt ggi igt a-3' SEQ ID NO:12
LP-654 5'-ttt gtg ggg tga ata tgg cag-3' SEQ ID NO:13
Uni (reverse) 5'-acg ggt acg acg ttc agg-3' SEQ ID NO:14
At site position number 19816 (forward) in Lambda Phage:
Priming site 5'-agtacgGTCAGTacagtGTCATctgcaggt-3' SEQ ID NO:15
FM-816 5'-acc cgc tat ctg tgc aii act gac-3' SEQ ID NO:16
BM-816 5'-iga tga cic gca cag ata gcg gg-3' SEQ ID NO:17
PR1-816 5'-gct atc tgt gca ggi tii ccg-3' SEQ ID NO:18
PR2-816 5'-gtc tgt gca ggg gtg gii gta-3' SEQ ID NO:19
LP-816 5'-cca gga tga gc tgt act gac-3' SEQ ID NO:20
Uni (forward) 5'-acc cgc tat ctg tgc agg-3' SEQ ID NO:21
At site position number 20397 (forward) in Lambda Phage:
Priming site 5'-tcatcaGAAACGaacgcATCATCaagtgcc-3' SEQ ID NO:22
FM-20397 5'-acc cgc tat ctg tgc aii cgt ttc-3' SEQ ID NO:23
BM-20397 5'-iga tga tic gea cag ata gcg gg-3' SEQ ID NO:24
PR1-20397 5'-agc tat ctg tgc agg iit iic tg-3' SEQ ID NO:25
PR2-20397 5'-gtc tgt gca ggg gtg gii gat-3' SEQ ID NO:26
LP-20397 5'-act tga tga tgc gtt cgt ttc t-3' SEQ ID NO:27
Uni (forward) 5'-acc cgc tat ctg tgc agg-3' SEQ ID NO:28

MATERIALS

Oligonucleotides were supplied by Genosys (Texas, USA). Sequenase and its reaction and dilution buffers were supplied by Amersham (UK manufactured for Amersham by former United States Biochemicals, Cleveland, Ohio, USA)

and AmpliTaq by Perkin-Elmer (California, USA; manufactured for Perkin Elmer by Roche Molecular Systems, Inc., NewJersey, USA). Deoxribonucleotide triphosphates were from Pharmacia LKB (Sweden). Expand buffers were from the Expand Long Template PCR kit of Boehringer Mannheim (Indiana, USA). Template DNA used was Lambda Phage DNA purchased from Promega (Madison, Wis., USA).

PRODUCT SIZES

The 2 forward and 2 reverse priming sites listed above can give 4 possible PCR products (that is each product having one forward and one reverse priming site). As their site position numbers suggest, the sizes of these products are 204, 479, 765, and 1060 bp. All of these products have been obtained using branched primer PCR as follows.

INITIAL EXTENSION

Initial extension reactions were performed as follows: the front module (10 pmole) and the back module (25 pmole) of the first (forward) branched primer were combined with the Lambda Phage template DNA (0.5 to 50 fmol) in a total reaction mix of 10 ul containing also 1X Sequenase reaction buffer, 50 uM each DATP, dCTP, dGTP and dTTP, and 10 mM DTT. The mixture was heated to 96° C. for 3–5 min to denature the DNA, then brought to 30° C., at which temperature the first initial extension reaction was started by adding 2 ul of Sequenase (diluted 1:8 in Dilution Buffer). Incubation at this temperature was continued for a further 1 min, then the reaction was heated at the rate of 0.4° C. per second to 42° C. where it was held for 5 min, before being raised to 65° C. for 5 min to inactivate the polymerase (Sequenase). The procedure was repeated after the addition of the second (reverse) branched primer, fresh Sequenase being again added following denaturation (to perform the second initial extension). If a thermostable polymerase is used in the initial extension (AmpliTaq and Stoffel Fragment may be suitable) there is no need to add fresh polymerase again after the denaturation stage. Optionally both the first and second (forward and reverse) branched primers were added before the first initial extension. When the reaction was completed, 40 ul of water was added to dilute the extension products.

PCR AMPLIFICATION (WITH PROOFREADING BY PR1S)

PCR reactions were carried out in a total volume of 25 ul, using Expand Buffer I (1X) from Boehringer-Mannheim. The concentration of each PR1 and/or other amplification primer was 0.3 uM, unless otherwise stated. (When PCR was performed without proofreading, universal stem-like primers, Uni, or the front modules themselves were used as amplification primers.) The template was a 1 ul aliquot of the product of the two initial extension reactions (diluted as described above), and dNTPs were added to 350 uM of each. High stringency PCR amplification began using hot start at 72° C. for 5 min, during which 2 ul AmpliTaq (diluted 1 in 8 in water and pre-heated) was added. This was followed by a denaturation step of 96° C. for 2.5 min and 25–30 cycles of: denaturation at 96° C. for 1 min, annealing at 56° C. for 1 min and extension at 72° C. for 1–4 min (depending on the size of the product). (All the above times are for block control mode of the thermocycler.)

FURTHER PROOFREADING BY PCR WITH PR2S

"Sequential mode", also termed "series of reactions" and "case A": A 1 ul aliquot of a 1 in 400 dilution of a completed PCR amplification using PR1 (described above) was used as the template. Two PR2s (forward and reverse) were used as the amplification primer pair.

"One-tube reaction", also termed "case B" (Here proofreading by PR1 and PR2 is carried out in the same PCR amplification):

An aliquot from an initial extension was used as the template (as in the case of amplification by PR1 alone, as described above), but here both PR1s and PR2s (for the same site) were used together as amplification primers, at a ratio of 1 to 10 (i.e. 0.03 uM PR1 and 0.3 uM PR2). In both cases (A and B) the conditions and temperature regimes were as described above for amplification with PR1s only.

Labels, Tags and Chemical Modifications

The modular primers and the amplification primers (e.g., PR, Uni) can be used with many labels and tags used with conventional primers. They can be made radioactive prior to the sequencing reaction, for example by phosphorylation with radioactive phosphate $^{32}P$. In other embodiments different isotopes, like $^{35}S$ can be used. For some automated sequencing machines the front module PR, or Uni (stem-like) primer can carry a fluorescent label near its 5'-end. For chemiluminescent detection they can carry a tag (a chain of atoms) with a binding group, like biotin, sitting on it. Alternatively, the binding group can be a chemical functional group, like an amino group, or carboxyl group, which can covalently bind various molecules. Biotin binding group can later bind a chemiluminescent molecule in a standard procedure of chemiluminescent detection. The biotin attached to the front module can also be used to bind streptavidin for DNA trapping electrophoresis (Ulanovsky et al. 1990).

An oligonucleotide library, as well as a single oligonucleotide can comprise one or more of these labels, tags and modifications. The labeled or modified oligonucleotide libraries can be built in more than one way. The modification, the tag or the label can be:

1. incorporated into the oligonucleotide during the synthesis of the oligonucleotide (e.g. biotin, aminomodifier II Glenn Research Corp.).
2. chemically linked to the oligonucleotide after the synthesis (biotinylation of the primary amino group incorporated during the synthesis);
3. enzymatically incorporated into the oligonucleotide after the synthesis of the oligonucleotide (e.g. terminal transferase mediated incorporation of dideoxy nucleotide triphosphate or of biotinylated dNTP).

The modular primer can be composed of a different number of oligonucleotides, which can have different sequences, from the examples above. The invention should not be limited to DNA and should include the possibility of one or both strands of the above description being RNA strands, as well as the nucleic acid polymerases being not only DNA but also RNA polymerases. The number of nucleotides (bases) in each part of each oligonucleotide shown here can be different from the examples described in this application.

The following notations are used herein:

A-deoxyadenine
C-deoxycytosine
G-deoxyguanine
T-deoxythymine
i-deoxyinosine
N-degenerate position (A+C+G+T)
X-specific (non-egenerate) position.

Documents Cited

Azhikina et al. (1993) *PNAS* 90:11460–11462.
Beskin, A. D., Zevin-Sonkin, D., Sobolev, I. A. & Ulanovsky, L. E. (1995) *Nucleic Acids Res.* 23:2881–2885.
Blöcker, H. & lincoln, D. N. (1994) *CABIOS* 10:193–197.
Egholm, M. et al. (1993) *Nature* 366:56–6568.
Guo, Z. (1997) *Nature Biotechnol.* 15:331–335.Kieleczawa, J., Dunn, J. J., & Studier, F. W. (1992) *Science* 258:787–1791.
Kotler, L., Sobolev, I. & Ulanovsky, L. (1994) *BioTechniques* 17:554–559.
Kotler, L. E., Zevin-Sonkin, D., Sobolev, I. A., Beskin, A. D., & Ulanovsky, L. E. (1993) *Proc. Natl. Acad. Sci. USA* 90:4241–4245.
Leontis, N. B., Kwok, W. & Newman, J. S. (1991) *Nucleic Acids Res.* 19:759–766.
McCombie, W. R. & Kieleczawa, J. (1994) *BioTechniques* 17:574–579.
Nielsen P. E. et al. (1991) *Science* 254:1497–1500.
Ohtsuka, E., Matsuki, S., Ikehara, M., Takahashi, Y. & Matsubara, K (1985) *J. Biol. Chem.* 260:2605–2608.
Raja et al. (1997) *Nucleic Acids Research* 25:800–805.
Studier, F. W. (1989) *Proc. Natl. Acad. Sci. USA* 86:6917–6921.
Szybalski, W. (1990) *Gene* 90:177–178.
Ulanovsky, L., et al. (1986) *Proc. Natl. Acad. Sci. USA* 83:862–866.
Ulanovsky, L. and Trifanov, E. (1987) *Nature* 326:720–722.
Ulanovsky, L. et al. (1990) *Nature* 343:190–192.
Walker T. G., et al. (1992) *Nucleic Acids Res.* 20:1691–1696.
Walker T. G. (1993) PCR Methods and Applications 3:1–6.

---

What is claimed is:

1. A composition of matter comprising:
   (a) a collection of front oligonucleotide modules wherein each module comprises a stem segment that has a constant sequence that is the same from module to module and an arm segment that has a variable sequence that varies from module to module within the collection; and
   (b) a collection of back oligonucleotide modules wherein each module comprises a stem segment that has a constant sequence that is the same from module to module and an arm segment that has a variable sequence that varies from module to module within the collection, wherein, the constant sequence of the front modules is complementary to the constant sequence of the back modules.

2. The composition of matter of claim 1 wherein said collection of front and of back oligonucleotide modules contains at least 2% of all possible sequence variations of the variable sequences of the modules.

3. The composition of claim 1, wherein the back oligonucleotide modules comprise a modified 3' terminus that inhibits extension of said 3' terminus.

4. The composition of claim 1, wherein the variable sequence of the front and back oligonucleotide modules are each between about 3 to about 10 nucleotides in length and are the same length within a collection.

5. The composition of claim 1, wherein at least one of said modules contains at least one chemical modification of the naturally occurring nucleic acid structure.

6. The composition of claim 2, wherein all possible sequence variations comprise between about $4^3$ to about $4^{10}$ different sequences.

7. The composition of claim 1, wherein the front constant sequence and the back constant sequence are each from between about 3 to about 30 nucleotides in length.

* * * * *

UNITED STATES PATENT AND TRADEMARK OFFICE
CERTIFICATE OF CORRECTION

PATENT NO.   : 6,235,889 B1
DATED        : May 22, 2001
INVENTOR(S)  : Levy Ulanovsky Page 1 of 1

It is certified that error appears in the above-identified patent and that said Letters Patent is hereby corrected as shown below:

<u>Title page,</u>
Item [56], OTHER PUBLICATIONS, in the Azikina, T. et al. reference please delete "h" after "affinity"
In the first Ulanovsky, L. reference please change "Circulation" to -- Circularization --
In the Watson, J.D. et al. reference please add -- (1987) -- after "et al."
In the McCombie, W.R. reference please correct the name of the second inventor from "Kieleczaws" to -- Kieleczawa --

Signed and Sealed this

Thirtieth Day of April, 2002

Attest:

JAMES E. ROGAN
*Attesting Officer*       *Director of the United States Patent and Trademark Office*